United States Patent [19]

Hillebrenner

[11] Patent Number: 5,470,548
[45] Date of Patent: Nov. 28, 1995

[54] SYSTEM FOR STERILIZATION OF OBJECTS

[75] Inventor: H. William Hillebrenner, Apex, N.C.

[73] Assignee: American Sterilizer Company, Erie, Pa.

[21] Appl. No.: 290,567

[22] Filed: Aug. 15, 1994

Related U.S. Application Data

[62] Division of Ser. No. 57,755, May 7, 1993, Pat. No. 5,364,590.

[51] Int. Cl.⁶ .................................................. A61L 2/20
[52] U.S. Cl. ........................... 422/295; 422/119; 422/292
[58] Field of Search ............................. 422/28, 295, 292, 422/119; 435/311

[56] References Cited

U.S. PATENT DOCUMENTS

| 4,169,123 | 9/1979 | Moore et al. | 422/29 |
|---|---|---|---|
| 4,169,124 | 9/1979 | Forstrom et al. | 422/33 |
| 4,239,730 | 12/1980 | Fahlvik et al. | 422/295 |
| 4,512,951 | 4/1985 | Koubek | 422/33 |
| 4,642,165 | 2/1987 | Bier | 422/28 |
| 5,217,698 | 6/1993 | Siegel et al. | 422/292 |

FOREIGN PATENT DOCUMENTS

| 0452780 | 10/1991 | European Pat. Off. | 422/28 |
|---|---|---|---|
| 2105591 | 3/1983 | United Kingdom . | |
| WO9317727 | 9/1987 | WIPO . | |
| WO8804939 | 7/1988 | WIPO . | |

*Primary Examiner*—Robert J. Warden
*Assistant Examiner*—Theresa T. Snider
*Attorney, Agent, or Firm*—Jones, Day, Reavis & Pogue

[57] ABSTRACT

An apparatus of remote temperature sensing for a gas heated chamber utilizing temperature sensors is disclosed, wherein at least a first temperature sensing device is coupled to an enclosed environment of a cabinet containing a sterilization cassette and at least a second temperature sensing device is coupled to a gas exit conduit from the cassette so as to avoid condensation on the internal walls of the cassette or on the object contained therein.

1 Claim, 1 Drawing Sheet

SYSTEM FOR STERILIZATION OF OBJECTS

This is a divisional of application Ser. No. 08/057,755 filed on May. 7, 1993, now U.S. Pat. No. 5,364,590.

FIELD OF THE INVENTION

The present invention relates generally to a sterilizing system and in particular to an improved system for sterilizing objects such as endoscopes in which the sterilized endoscope is retained within the cassette in which it was sterilized until ready for use, thus avoiding any contamination by exposure to the atmosphere or handling before use. The present system provides a method to improve sterilization by avoiding condensation of moisture or sterilant on an object contained in a sterilization holding cassette or the walls of such a cassette prior to, during or after sterilization.

BACKGROUND OF THE INVENTION

Contamination by microorganisms is one of the most troublesome problems encountered in hospitals and clinics today and there is often a need to sterilize devices such as medical instruments and the like. In particular, the rapid succession of medical examinations of patients called for by modern methods of clinical health practice requires continuous sterilization of numerous devices in succession; this is particular true with endoscope devices.

In U.S. Pat. Nos. 4,169,123 and 4,169,124 cold gas sterilization using hydrogen peroxide gas at temperatures below 80° C. is disclosed. The liquid hydrogen peroxide is vaporized and the hydrogen peroxide vapor is then introduced into the sterilization chamber by pressure differential.

U.S. Pat. No. 4,642,165 discloses a method of injecting and vaporizing successive increments of a multicomponent liquid such as an aqueous solution of hydrogen peroxide, for delivery into a vacuum chamber. The vacuum in the chamber draws the multicomponent vapor into the chamber.

U.S. Pat. No. 4,512,951 discloses a method of liquid contact hydrogen peroxide sterilization. Goods to be sterilized are maintained in the sterilization chamber at a temperature below the dew point of the vapor sterilant. An aqueous solution of hydrogen peroxide is vaporized and passed into the evacuated sterilization chamber were, upon contact with the goods, the vapor condenses to form a liquid layer of sterilant on the goods. A vacuum in the chamber draws the vapor into the chamber.

United Kingdom Patent No. 1,582,060 discloses a similar liquid contact hydrogen peroxide sterilization method operated without a vacuum chamber. Liquid hydrogen peroxide is pumped through an ultrasonic spray nozzle which is operated by a stream of dehydrated air. A mist of hydrogen peroxide is sprayed into a container and mixed with hot air to change the mist into a vapor. The vapor is piped into a non-pressurized sterilization chamber where it condenses on a cool moving web of material. A stream of hot air in an adjacent chamber removes the hydrogen peroxide layer from the web. The stream is then passed to a water separator where it is relieved of the sterilant.

U.S. patent application Ser. No. 07/851,096, now abandoned, incorporated by reference herewith, discloses the use of a sealable cassette in which the endoscope or other object is placed. The cassette has input and output fluid sealing ports for the introduction and removal of sterilizing fluid. The endoscope or other medical instrument, if hollow, is coupled with to the input or output port. The cassette is formed of two identical halves which are placed in superimposed sealable relationship with each other to form a hollow chamber. A latch is placed on one or more handles on the cassette to create a pre-sealing condition to allow a vacuum to be introduced at the outlet part.

The cassette is then placed in an outer-oven-like container or warming chamber or cabinet where the temperature is properly maintained. Connections are made to open the input and output ports on the cassette such that the sterilizing agent may be introduced through a first port to bathe the outside of the medical instrument or other object, such as an endoscope, while one end of the hollow object, such as an endoscope, is coupled to the output port where a vacuum is supplied external to the cassette to pull the sterilization agent into the cassette and through the interior passage ways of the hollow object.

U.S. patent application Ser. No. 07/851,096, now abandoned, further teaches a system for sterilizing an object comprising a hollow cassette for containing the object, the cassette having an opening section for ingress and egress of the object, sealing means for forming a fluid-tight seal around the opening section, input and output ports in the cassette for receiving and exhausting a sterilizing fluid, and a sealing check valve in the input and output ports for providing a fluid-tight seal when connections are made to the input and output ports such that when the object is sterilized within the cassette, the cassette will maintain a sterilized atmosphere for the object until the cassette is opened to allow use of the object.

It is necessary to know the temperature within the casing or holding cassette to insure optimum sterilization. Current methods of temperature measurement using the cassette and system described U.S. patent application Ser. No. 07/851,096, now abandoned, include having a temperature sensor connected directly to either the object to be sterilized or the casing or cassette holding the object. The temperature sensor or associated wiring is attached to the holding cassette at each use and then disconnected. This level of handling is inconvenient and provides an increased opportunity for damage to the sensor.

Additionally, if vapor sterilant is used to sterilize the particular object (e.g. endoscopes, steel or plastic light guides, scissors, hemostats, camera cords etc.) it is not only desirable to know the internal temperature of the holding cassette so that the sterilant can be introduced thereto at the appropriate temperature to optimize the partial pressure of the sterilant in the gas, thereby optimizing the kill rate, but it is also desirable to know the internal temperature of the cassette with respect to the surrounding environment to prevent condensation of moisture in the air within the cassette. It is important to avoid having sterilant vapor condense onto the particular object to be sterilized or on the walls of the cassette in order to insure the proper level of sterilization and to avoid any degradation that may take place by a liquid sterilant contacting the cassette or object contained therein.

There is a need for a method which can measure the temperature of an object in a remote manner such that direct contact with the sensing device and the object, casing or holding cassette is not necessary and while providing accurate knowledge of the internal temperature.

SUMMARY OF INVENTION

It is therefore a main object of the present invention to provide a method of effectively measuring the temperature of an object, casing or holding cassette contained in a chamber or cabinet in a remote manner without requiring direct physical contact with the object, casing or holding cassette, thereby avoiding condensation of moisture or vapor sterilant. Furthermore, by maintaining the optimal temperature within the cassette, the optimal partial pressure of sterilant vapor is maintained during sterilization.

It is also an important object of this invention to sterilize an object and the internal area of the object holding cassette while avoiding condensation therein that can prevent proper sterilization and/or degrade or corrode any materials on which condensation might otherwise have occurred.

Additional objects and advantages of the invention will be set forth in part in the description that follows, and in part will be obvious from the description, or may be learned by practice of the invention. The objects and advantages of the invention may be realized and obtained by means of instrumentalities and combinations particularly pointed out in the appended claims.

To achieve these objects and in accordance with the purpose of the invention, the present invention provides a system comprising:

a) a hollow cassette for containing the object;

b) the cassette having a closable access for ingress and egress of the object;

c) a sealing means for forming a fluid-tight seal around the access to the cassette when closed;

d) input and output ports in the cassette for receiving and exhausting air and sterilant vapor;

e) carrier means for transporting air and sterilant vapor gases into and out of the cassette through the input and output ports;

f) a warming cabinet for containing the hollow cassette having a first input and a first output port coupled to the carrier means for providing air and sterilant to the input and output ports of the cassette;

g) a second input and a second output port in the warming cabinet for receiving and exhausting air;

h) a first temperature sensing device having a temperature sensing portion extended into the interior of the warming cabinet for sensing as a first temperature, the temperature of the internal cabinet environment outside of the cassette; and i) a second temperature sensing device coupled to the carrier means for sensing as a second temperature the gas exiting the cassette such that the first and second temperatures can be maintained so as to prevent condensation of moisture on the internal walls of the cassette or on the object contained therein.

The method of the present invention is achieved by heating the chamber or cabinet by an external source. When the temperature of the internal atmosphere of the cabinet has stabilized at a desired temperature determined empirically, the object containing cassette is placed inside the cabinet. The temperature of the internal atmosphere of the cabinet is indicated by the first temperature sensing device extended within the cabinet. The temperature of the chamber atmosphere will drop when the cassette is placed inside and, accordingly, additional heat will needed to be provided to raise the temperature to the desired level.

Warm gas, such as air, is inserted or forced into and exit from the sterilization cassette through the carrier means, such as an inlet gas line and exit gas line. These lines pass through input and output ports located in the chamber. The exit gas line has a second temperature sensing device coupled thereto for indicating the temperature of any gas in said exit line. When the temperature of the chamber atmosphere and the gas in the cassette exit line reaches predetermined temperatures, sterilization of the cassette and the object contained therein will be effective without the sterilant or moisture forming condensation. Sterilant vapor is then introduced into the cassette via the inlet gas line to the cassette to effectuate sterilization. The first and second temperature sensing devices are monitored to allow heat to be added to insure that the predetermined temperatures are maintained. The temperature sensing devices suitable for use in this invention are well known and include thermocouples.

BRIEF DESCRIPTION OF THE DRAWINGS

The present invention can best be understood by reference to the drawings, in which.

DETAILED DESCRIPTION OF THE PREFERRED EMBODIMENT

Figure 1:
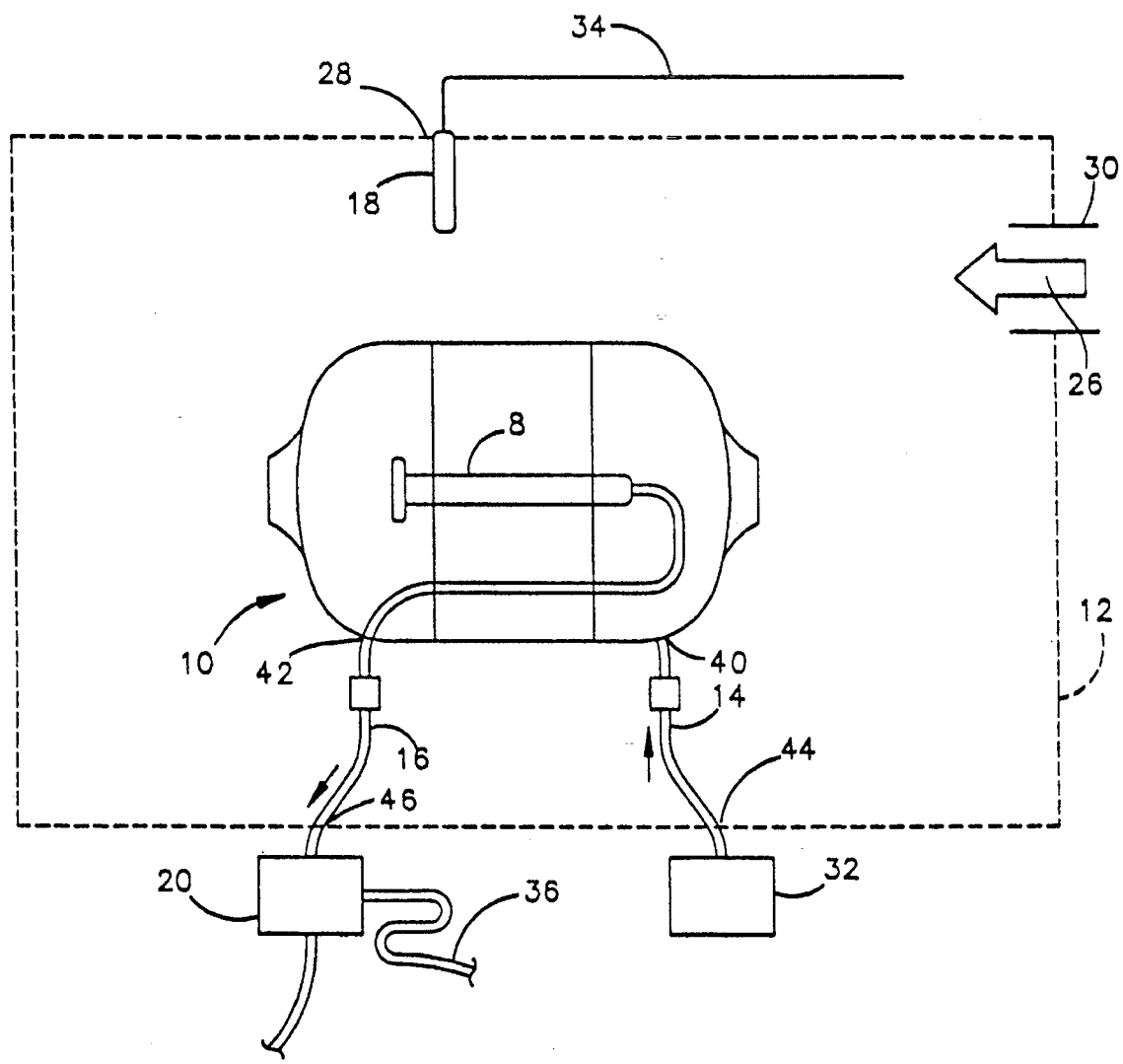
FIG. 1 is a schematic diagram of a preferred embodiment of a system for practicing the method of the present invention.

The present invention overcomes the disadvantages of current temperature measurement methods for cassette sterilization by using at least two remote temperature sensors to determine the temperature differential between gas emanating from the object casing or holding cassette and the internal cabinet environment surrounding the cassette.

The invention will first be described in reference to FIG. 1, which illustrates components of a system for practicing a preferred embodiment of the invention. The system, as depicted in FIG. 1, includes a cassette 10, warming cabinet 12, air conduits 14 and 16 and 26 and 28, temperature sensors 18 and 20, external heat source 30 and heat/sterilant source 32. The conduits 14, 16 connect with the cassette 10 at respective input and output ports 40, 42 in the cassette for receiving and exhausting air and sterilant vapor. The conduits 14, 16 connect with the cabinet 12 at respective second input and output ports 44, 46, mounted on the interior surfaces of the cabinet 12, for receiving and exhausting air and sterilant vapor.

Warming cabinet 12 is heated to a desired temperature by the external heat source 30, through conduit 26. The cabinet atmosphere temperature is indicated by temperature sensor 18. The object(s) 8 to be sterilized are placed within cassette 10 which, in turn, is placed inside warming cabinet 12. Conduit 14 allows hot air (and sterilant) to flow into cassette 10 and warms the object(s) 8 to an appropriate temperature level, while conduit 16 allows the air (and sterilant) to flow out of cassette 10. In the mean time, external heat source 30 continues to heat the cabinet atmosphere and warm air flows around the outside of the cassette in warming cabinet 12.

Temperature sensor 20 is coupled to conduit 16 so as to indicate the temperature changes of exhaust air from cassette 10. Similarly, temperature sensor 18 is extended within warming cabinet 12 in order to indicate the temperature changes within warming cabinet 12. The initial temperatures detected with sensors 18 and 20 typically drop when cassette 10 and the enclosed object(s) are placed inside the system due to the initial lower temperatures of the cassette and enclosed object. As the temperature of the cassettes and object 8 within rises, sensors 18 and 20 reflect the temperature increases. Cassette 10 is allowed to warm until a predetermined temperature achieved. The optimum temperature indicated by sensors 18 and 20 to begin the sterilant injection (and hence, the sterilization cycle) can be determined empirically for any object placed within cassette 10 and any desired sterilant. The temperature parameters change depending on the vapor sterilant used; quantity of sterilant; and the absolute temperature and partial pressure of the sterilant in air, all of which affect, the kill rate achieved by the sterilant and the dew point or condensation temperature of the vapor. The preferred temperature differential between temperature sensors 18 and 20 is approximately zero, more preferred is temperature differential is in the range of from 0° to 10° F. It is important that neither temperature indicated by sensors 18 and 20 vary too far from the optimal temperature. Too low a temperature by either sensor and condensation may occur within the sterilization cassette. Too high a temperature and the partial pressure of the sterilant within the cassette may be lowered, affecting the sterilant's ability to sterilize the inside of the cassette and/or the object contained therein.

Once the desired temperature is obtained, sterilant can be introduced into the cassette via inlet line 14 from the external source 32. Wires and controls (34 and 36) are coupled to the temperature sensors 18, 20 to enable remote reading of the temperatures.

EXAMPLE

In the sterilization of endoscopes, the cabinet 12 atmosphere is heated with air for about 15 minutes until temperature sensor 18 indicates a temperature of between about 100°–102° F., optimally, and not more than about 110° F. The temperature can be controlled by the addition of heat via external heat source 30. The endoscope is placed in the holding cassette which is then placed inside cabinet 12. Heated air is supplied to the holding cassette via gas line 14 and is removed via exit line 16. When temperature sensors 18 and 20 indicate temperatures of between about 100° and 102° F., optimally, and not more than about 110° F., the internal cassette temperature has reached the optimum temperature and the sterilization cycle can begin using vapor hydrogen peroxide that is vaporized from a liquid having a weight percent of 30–35% hydrogen peroxide, which is introduced into the cassette through inlet line 14, from an external source 32. The temperature is sufficient that condensation is avoided on both the endoscope and the internal walls of the cassette. By continuing to monitor the temperature sensors, the desired temperatures and temperature differential can be maintained prior to, during and after sterilization to avoid condensation of either moisture or the vapor sterilant any where within the cassette.

While this invention has been described in connection with preferred embodiments, it is not intended to limit the scope of the invention to particular embodiments set forth, but, to the contrary, it is intended to cover such alternatives, modifications, and equivalents as may be included within the spirit and scope of the invention as defined by the appended claims.

What is claimed is:

1. A system for sterilizing an object comprising:

a hollow cassette for receiving the object;

input and output ports in the cassette for receiving and exhausting air and sterilant vapor;

carrier means for transporting air and sterilant vapor into and out of the cassette through the input and output ports;

a cabinet for containing the hollow cassette having a first input and a first output ports coupled to the carrier means for providing air and sterilant vapor to the input and output ports of the cassette;

a second input and a second output ports, mounted on the interior surfaces of the cabinet for receiving and exhausting air and sterilant vapor;

a first temperature sensing device extended into the interior of the cabinet for sensing as a first temperature, the temperature of the internal cabinet environment outside of the cassette when the cassette is inserted within the cabinet;

a second temperature sensing device, located downstream from the cassette, and coupled to the carrier means for transporting air and sterilant vapor out of the cassette for sensing as a second temperature the temperature of gas exiting the cassette such that the first and second temperatures can be maintained so as to prevent condensation of moisture on the walls of the cassette and on the object therein.

* * * * *